(12) United States Patent
Speiser et al.

(10) Patent No.: US 7,199,075 B1
(45) Date of Patent: Apr. 3, 2007

(54) ORGANOMETALLIC COMPLEXES THAT COMPRISE BIDENTATE CHELATING LIGANDS THAT COMBINE A NITROGEN-CONTAINING HETEROCYCLIC COMPOUND WITH AN ALCOHOL AND THEIR USE FOR CATALYZING THE OLIGOMERIZATION OF OLEFINS

(75) Inventors: Fredy Speiser, Hambourg (DE); Pierre Braunstein, Strasbourg (FR); Lucien Saussine, Croissy sur Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 581 days.

(21) Appl. No.: 10/446,164

(22) Filed: May 28, 2003

(30) Foreign Application Priority Data

May 28, 2002 (FR) .................................. 02 06476

(51) Int. Cl.
B01J 31/00 (2006.01)
B01J 37/00 (2006.01)
C08F 4/02 (2006.01)
C08F 4/60 (2006.01)
C07C 2/02 (2006.01)

(52) U.S. Cl. ...................... 502/117; 585/522; 585/523; 585/527

(58) Field of Classification Search ................ 502/117; 582/522, 523, 527
See application file for complete search history.

(56) References Cited

U.S. PATENT DOCUMENTS

| 3,625,927 | A | * | 12/1971 | Yoshimoto et al. | ......... 525/338 |
| 3,644,218 | A | * | 2/1972 | Dunn | .......................... 502/117 |
| 4,000,211 | A | | 12/1976 | Smith et al. | |
| 4,069,273 | A | | 1/1978 | Komoto | |
| 6,309,997 | B1 | * | 10/2001 | Fujita et al. | ................ 502/167 |
| 6,399,724 | B1 | * | 6/2002 | Matsui et al. | ............... 526/161 |
| 6,864,205 | B2 | * | 3/2005 | Murray | ....................... 502/103 |

| 2002/0107345 | A1 | * | 8/2002 | Ittel et al. | ................... 526/161 |

FOREIGN PATENT DOCUMENTS

WO    WO 99/54364    * 10/1999

OTHER PUBLICATIONS

C. Bolm et al. "Catalytic enantioselective conjugate addition of dialkylzinc compounds to chalcones" Chemich Berichte., vol. 125, 1992, pp. 1205-1215, XP002227949 Verlag Chemie GmbH. Weinheim., DE ISSN: 0009-2940.
Desjardins S y et al.: "Insertion into the nickel-carbon bond of N—O chelated arylnickel (II) complexes. The development of single component catalysts for the oligomerisation of ethylene" Journal of Organometallic Chemistry, Elsevier-Sequoia S.A. Lausanne, CH vol. 515, No. 1. May 31, 1996, pp. 233-243, XP004036010 ISSN: 0022-328X.
Chemical Abstracts Service, Columbus Ohio, US; Golounin A.V. et al.: "Extractive power of mixtures of carboxylic acids and organic bases" retrieved from STN Database accession No. 1992: 461739 XP002227950.
"Synthesis of 2-(α-Hydroxyalkyl)-1,3-heterocyclic Alcohols and Aryl Carbamates", Lendon N. Pridgen and George Miller, pp. 1223-1230. J. Heterocyclic Chem. vol. 20, No. 1223 (1983).
"Transmission of Substituent Effects in Heterocyclic Systems, The Solvolysis of Some Substituted Chloroalkylpyridines", Donald S. Noyce and Joseph A. Virgilio, J. Org. Chem., vol. 38, No. 15, 1973, pp. 2660-2664.

* cited by examiner

Primary Examiner—J. A. Lorengo
Assistant Examiner—J. Pasterczyk
(74) Attorney, Agent, or Firm—Millen, White, Zelano & Branigan, P.C.

(57) ABSTRACT

A catalyst for the oligomerization of olefins, especially ethylene contains:
- at least one nickel complex e.g. $Li_2 Ni X_2$ that results from bringing into contact a nickel salt e.g. a nickel carboxylate with a bidentate chelating ligand containing a nitrogen-containing heterocyclic compound with an alcohol e.g. Ha-C(OH)RR'; and
- at least one hydrocarbylaluminum compound from tris (hydrocarbyl)aluminum compounds, chlorinated or brominated hydrocarbylaluminum compounds or at least one aluminoxane.

17 Claims, No Drawings

ORGANOMETALLIC COMPLEXES THAT COMPRISE BIDENTATE CHELATING LIGANDS THAT COMBINE A NITROGEN-CONTAINING HETEROCYCLIC COMPOUND WITH AN ALCOHOL AND THEIR USE FOR CATALYZING THE OLIGOMERIZATION OF OLEFINS

This invention relates to the oligomerization of olefins, in particular ethylene.

An object of the invention is to provide a new catalytic composition. Another object of the invention is to provide a process for oligomerization of olefins, in particular ethylene, using this catalytic composition.

It is well known that the monoolefins-$\alpha$, such as ethylene, propylene or butene-1, can be oligomerized with catalytic systems based on transition metals such as nickel, chromium, titanium, zirconium or other metals, in the presence of a co-catalyst such as a hydrocarbylaluminum compound, a hydrocarbylaluminum halide or an aluminoxane.

Several types of ligands for stabilizing the catalytic radical and for orienting the selectivity of the oligomerization reaction have been described. Phosphine-type ligands (U.S. Pat. No. 4,518,814 and U.S. Pat. No. 5,245,097) or bidentate ligands combine a phospine with an oxidized anion such as a carboxylate (U.S. Pat. No. 3,676,523, U.S. Pat. No. 4 472 522, U.S. Pat. No. 4,528,416, U.S. Pat. No. 5,557,027), or an enolate (W. Keim et al. Angew. Chem. [Applied Chemistry] Int. Ed. 1978, 17, 466, U.S. Pat. No. 4,293,727 and U.S. Pat. No. 4,310,716). Among these catalysts, some are used in an alcohol. To prepare the catalyst, it is possible to use zero valent nickel (for example bis (cyclooctadiene) nickel) as a starting material or to reduce nickel (II) salt by an alkylaluminum compound or a boron hydride.

More recently, the use of complexes that comprise monoanionic chelating ligands of salicylaldimine type were described by several groups (Grubbs et al., in Organometallics, 1998, 17, 3149–51; WO-A-98/30609) only for the polymerization of ethylene. These complexes are prepared by reaction of an organometallic compound of nickel with chelating ligands or anions that are derived therefrom. Nickel complexes prepared by reaction of picolinate anion on the Ni(o-tolyl)Br(PPh$_3$)$_2$ complex catalyze the oligomerization of the ethylene with a low activity (C4–C10 olefins: 75%-alpha-selectivity: 63%—K. S. Cavell et al. in J. Organomet. Chem. 1996, 515, 233–43).

It has now been found, unexpectedly, that a catalytic composition that comprises at least one nickel complex that contains at least one bidentate chelating ligand that combines a nitrogen-containing heterocyclic compound with an alcohol and at least one hydrocarbylaluminum compound or at least one aluminoxane, named activating agent here, exhibits an improved activity for the oligomerization of olefins, in particular ethylene.

The catalytic composition of the invention thus is defined as comprising:

At least one nickel complex that contains at least one bidentate chelating ligand that combines a nitrogen-containing heterocyclic compound with an alcohol; and At least one hydrocarbylaluminum compound that is selected from the group that is formed by the tris (hydrocarbyl)aluminum compounds and the chlorinated or brominated hydrocarbylaluminum compounds or at least one aluminoxane.

More specifically, the nickel complexes that are used in this invention have for general formula L$_2$NiX$_2$ in which:

L is a bidentate chelating ligand that combines a nitrogen-containing heterocyclic compound with an alcohol and corresponds to general formula:

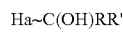

in which R and R', identical or different, each represent a monovalent hydrocarbon-containing radical that contains up to 12 carbon atoms, such as alkyl, aryl, aralkyl, alkaryl, cycloalkyl or substituted aryl, or a perfluoroalkyl radical, whereby nitrogen-containing heterocyclic compound Ha is selected from among the derivatives that comprise the pyridine, oxazoline or imidazole cycles, optionally substituted;

X can be an alkyl radical, a halide anion, Cl, Br or I, an acetylacetonate, acetate, or trifluoroacetate anion, or more generally a carboxylate anion R"COO$^-$ for which R" is a hydrocarbyl radical, for example, alkyl, cycloalkyl, alkenyl, aryl, aralkyl or alkaryl that contains up to 20 carbon atoms, preferably a hydrocarbyl radical with 5 to 20 carbon atoms, optionally substituted by halogen atoms (fluorine or chlorine). By way of nonlimiting examples, the carboxylate anion can be selected from among the following anions: octoate, ethyl-2-hexanoate, stearate, oleate, naphthenate and adipate.

More specifically, the nitrogen-containing heterocyclic compounds Ha can correspond to the general formulas below:

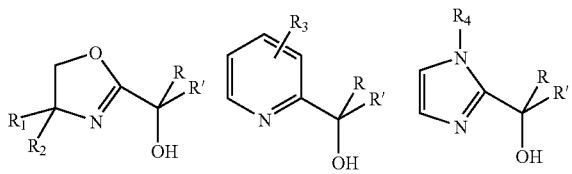

in which radicals R$_1$, R$_2$, R$_3$ and R$_4$, which can be identical or different, are selected from among the hydrogen atom, the linear or branched alkyl radicals, and the aryl, aralkyl or alkaryl radicals that comprise 1 to 12 carbon atoms. Radical R$_3$ can be in any of the free positions of the aromatic core. By way of nonlimiting examples, these substituents can be selected from among the methyl, ethyl, isopropyl, isobutyl, tert-butyl, cyclohexyl, phenyl and benzyl radicals.

Furthermore, in the formulas above, radicals R and R', R and R$_3$ or R and R$_4$ can be connected to one another and form part of the same cyclic radical.

For the L$_2$NiX$_2$ complexes, it is possible to cite the following complexes by way of nonlimiting examples:

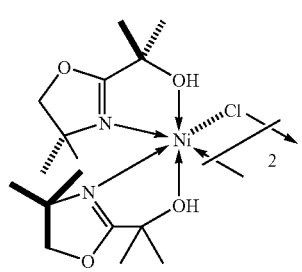

-continued

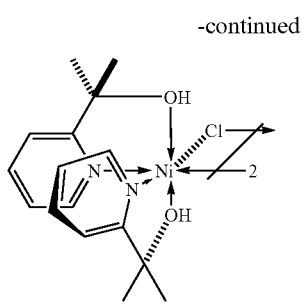

12

The preparation of the nickel complex $L_2NiX_2$ is carried out according to the methods that are known in the literature for the synthesis of nickel complexes with a neutral ligand. Any process for preparation of this compound can be suitable, such as, for example, the reaction of the ligand with a nickel salt in an organic solvent, for example an ether, an alcohol, or a chlorinated solvent, such as dichloromethane. The complex can be prepared in situ in the solvent that is used for the oligomerization reaction. In this case, the mixing order of the nickel salt and the ligand is not critical. However, it is preferred first to prepare a solution of a nickel salt that is soluble in an organic medium, such as, for example, a nickel carboxylate, and then to add the ligand.

As indicated above, the activating agent that is used can be:

Either a hydrocarbylaluminum compound that is selected from, for example, the group that is formed by the tris(hydrocarbyl)aluminum and the chlorinated or brominated hydrocarbylaluminum compounds;

Or an aluminoxane.

The tris(hydrocarbyl)aluminum compounds and the chlorinated or brominated hydrocarbylaluminum compounds preferably correspond to the general formula $AlR''_mY_{3-m}$ in which R'' represents a monovalent hydrocarbon-containing radical that contains, for example, up to 12 carbon atoms such as alkyl, aryl, aralkyl, alkaryl or cycloalkyl, Y represents a halogen atom that is selected, for example, from among chlorine and bromine, whereby Y is preferably a chlorine atom, and m assumes a value of 1 to 3, whereby m is preferably equal to 1. As examples of such compounds of formula $AlR''_mY_{3-m}$, it is possible to mention dichloroethyl aluminum, ethyl aluminum sesquichloride, chlorodiethyl aluminum, triethyl aluminum, dichloroisobutyl aluminum, chlorodiisobutyl aluminum, triisobutyl aluminum and tripropyl aluminum.

As an example of aluminoxane, it is possible to mention methylaluminoxane.

The nickel complex and the optional aluminum co-catalyst can be brought into contact in a solvent that consists of a saturated hydrocarbon, such as hexane, cyclohexane, heptane, butane or isobutane, by an unsaturated hydrocarbon such as a monoolefin or a diolefin that comprises, for example, 4 to 20 carbon atoms, or by an aromatic hydrocarbon such as benzene, toluene, ortho-xylene, mesitylene, ethylbenzene, or by a chlorinated hydrocarbon such as chlorobenzene or dichloromethane, pure or in a mixture.

The nickel concentration in the catalytic solution generally varies from $1 \cdot 10^{-5}$ to 0.1 mol/l, preferably from $5 \cdot 10^{-5}$ to $1 \cdot 10^{-2}$ mol/l.

The molar ratio between the optional hydrocarbylaluminum and the nickel complex is selected between 1/1 to 800/1, preferably from 5/1 to 500/1.

When the hydrocarbylaluminum compound is used, the mixing order of the two components of the catalytic composition is not critical. It is preferred, however, to add the hydrocarbylaluminum compound to the solution of the complex.

The invention also comprises a process for oligomerization of olefins, in particular ethylene, using the preceding catalytic composition.

The oligomerization reaction of the ethylene can be carried out under a total pressure of 0.5 to 15 MPa, preferably from 1 to 8 MPa, and at a temperature of from 20 to 180° C., preferably from 40 to 140° C.

In a particular embodiment of the intermittent oligomerization catalytic reaction, a selected volume of the catalytic solution, constituted as described above, is introduced into a reactor that is equipped with commonly used stirring, heating and cooling devices, then it is pressurized by ethylene to the desired pressure, and the temperature is adjusted to the desired value. The oligomerization reactor is kept at a constant pressure by introducing ethylene until the total volume of liquid that is produced represents, for example, 2 to 50×the volume of the catalytic solution that was originally introduced. The catalyst is then destroyed by any commonly used means that is known to one skilled in the art, then it is withdrawn, and the products of the reaction and the solvent are separated.

In the case of continuous operation, the implementation is, for example, as follows: the catalytic solution is injected at the same time as the ethylene into a reactor that is stirred by standard mechanical means or by an outside recirculation, and it is kept at the desired temperature. It is also possible to inject the components of the catalyst separately into the reaction medium. The ethylene is introduced by a pressure-controlled intake valve that keeps the pressure constant. The reaction mixture is drawn off with a valve that is controlled by the liquid level so as to keep the latter constant. The catalyst is continuously destroyed by any commonly used means that is known to one skilled in the art, then the reaction products as well as the solvent are separated, for example by distillation. The ethylene that has not been transformed can be recycled in the reactor.

The following examples illustrate the invention without limiting its scope.

EXAMPLE 1 a) Preparation of the (Oxazoline Alcohol)$_2$NiCl$_2$ Complex

The oxazoline alcohol ligand for which R1=R2=R=R'=methyl was prepared according to the methods that are described in the literature (L. N. Pridgen, G. M. Miller, J. Heterocyclic. Chem. 1983, 20, 1223).

The oxazoline alcohol ligand (0.700 g, 4.45 mmol) is put into solution in 30 ml of dichloromethane, then, after a half-equivalent of nickel-dimethoxy-1,2-ethane chloride, NiCl$_2$(DME) (0.474 g, 2.29 mmol) is added, the solution is stirred for 12 hours. The solution is filtered on Celite, then concentrated. The green-yellow solid is dissolved in 20 ml of toluene, then precipitated by the addition of hexane, filtered, and dried under vacuum. Yield: 0.911 g, or 75%. This product is characterized by an infrared absorption band at 1662 cm$^{-1}$, characteristic of the C=N double bond that is coordinated with nickel.

b) Oligomerization of Ethylene

In a 100 ml glass flask that is placed under an inert atmosphere, $0.063 \cdot 10^{-3}$ mol of nickel complex that is diluted with 60 ml of distilled toluene and that is kept under an inert atmosphere is introduced in the absence of air and moisture.

In a stainless steel autoclave with a useful volume of 100 ml, equipped with a double jacket that makes it possible to regulate the temperature by circulation of oil, there is introduced, in order, under an ethylene atmosphere and at ambient temperature, 10 ml of the solution of the nickel complex that is prepared above, or $1.05 \cdot 10^{-5}$ mol of nickel and $2.1 \cdot 10^{-3}$ mol of methylaluminoxane in solution in 10 ml of toluene. The temperature is then brought to 30° C., and the ethylene pressure is kept at 1 MPa.

After 35 minutes of reaction, the introduction of ethylene is stopped, and the reactor is cooled and degassed, then the gas and the liquid that have been drawn off by means of a syringe are analyzed by vapor phase chromatography. The products consist for the most part of alpha-olefins. The composition of the mixture is provided in Table 1.

EXAMPLE 2

In the same device as the one that was used for Example 1 and under the same conditions, except that the methylaluminoxane to nickel ratio is 400/1 instead of 200/1. The composition of the products is provided in Table 1.

EXAMPLE 3 a) Preparation of the Nickel Complex

For the synthesis of the complex, the operation is carried out as in Example 1, except that the pyridine alcohol ligand is used (with R=R'=methyl, $R_3$=H).

Synthesis of the pyridine alcohol ligand: it is prepared according to the operating procedure described by Noyce et al. in J. Org. Chem. 1973, 38, 2260.

b) Oligomerization of the Ethylene

The operation is carried out in the same device as the one that was used for Example 1 and under the same conditions. The methylaluminoxane to nickel ratio is 200/1. The composition of the products is given in Table 1.

EXAMPLE 4

The operation is carried out as in Example 3, except that the aluminoxane to nickel ratio is 400/1 instead of 200/1.

EXAMPLE 5

The operation is carried out in the same device as the one that was used for Example 1 and under the same conditions, except that the activating agent is dichloroethyl aluminum with a dichloroethyl aluminum to nickel molar ratio of 6/1.

EXAMPLE 6

The operation is carried out in the same device as the one that was used for Example 1 and under the same conditions, except that the complex of Example 3 is used and the activating agent is dichloroethyl aluminum with a dichloroethyl aluminum to nickel molar ratio of 6/1.

TABLE 1

| Example | Distribution of the Oligomers (% by Weight) | | | Productivity (g of ethylene/g of Ni/h) |
|---|---|---|---|---|
| | C4 | C6 | C8 | |
| 1 | 87.5 | 10.5 | 2.0 | 7410 |
| 2 | 84.0 | 13.7 | 2.3 | 8920 |
| 3 | 87.0 | 11.5 | 1.5 | 5000 |
| 4 | 82.6 | 14.8 | 2.5 | 6800 |
| 5 | 70.4 | 27.6 | 1.9 | 83300 |
| 6 | 64.2 | 32.6 | 3.1 | 46400 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius, and all parts and percentages are by weight, unless otherwise indicated.

The entire disclosures of all applications, patents and publications, cited herein and of corresponding French Application No. 02/06,476, filed May 28, 2002, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst composition comprising at least one nickel complex corresponding to general formula $L_2NiX_2$ in which:
   L is a bidentate chelating ligand that contains a nitrogen-containing heterocyclic compound of general formula:

Ha-C(OH)RR' in which:
   R and R', identical or different, each represent a monovalent radical that contains up to 12 carbon atoms wherein such monovalent radical is alkyl, aryl, aralkyl, alkaryl, cycloalkyl or a substituted aryl radical, or a perfluoroalkyl radical,
   Ha represents a radical wherein said radical is an unsubstituted or substituted pyridine, oxazoline or an imidazole cycle;
   and X is an alkyl radical, a halide anion, acetylacetonate or a carboxylate optionally substituted by at least one halogen,
   said catalyst composition further comprising at least one hydrocarbylaluminium compound which is at least one tris(hydrocarbyl)aluminum compound or at least one chlorinated or brominated hydrocarbylaluminum compound or at least one aluminoxane.

2. A catalyst composition according to claim 1, wherein the hydrocarbylaluminum compound is dichloroethylaluminum.

3. A catalyst composition according to claim 1, wherein Ha is an unsubstituted or substituted pyridine, oxazoline or N-methylimidazole radical.

4. A catalyst composition according to claim 3, wherein the bidentate chelating ligand corresponds to one of the formulas:

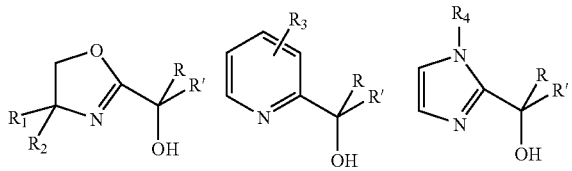

in which radicals $R_1$, $R_2$, $R_3$ and $R_4$, identical or different, are a hydrogen atom, a member having 1–12 carbon atoms being a linear or branched alkyl radical, an aryl, an aralkyl or an alkaryl radical.

5. A catalyst composition according to claim 1, wherein X is a Cl, Br, I, acetylacetonate, acetate or trifluoroacetate anion.

6. A catalyst composition according to claim 1, wherein the hydrocarbylaluminum compound is at least one of dichloroethyl aluminum, ethyl aluminum sesquichloride, chlorodiethyl aluminum, triethyl aluminum, dichloroisobutyl aluminum, chlorodiisobutyl aluminum, triisobutyl aluminum, tripropyl aluminum, or methylaluminoxane.

7. A catalyst composition according to claim 6, containing methylaluminoxane.

8. A catalyst composition according to claim 1, wherein the components of the catalyst are brought into contact in a solvent comprising an olefinic or aromatic unsaturated or saturated hydrocarbon.

9. A catalyst composition according to claim 8, wherein the concentration of nickel in the catalytic solution is $1 \cdot 10^{-5}$ to 0.1 mol/l.

10. A catalyst composition according to claim 1, wherein the molar ratio between hydrocarbylaluminum compound and the nickel complex is 5/1 to 500/1.

11. A catalytic process comprising oligomerization of ethylene wherein the catalyst is the catalyst composition according to claim 1.

12. A process according to claim 11, wherein the oligomerization reaction of the ethylene is carried out under a pressure of 0.5 to 15 MPa and at a temperature of 20 to 180° C.

13. A catalyst composition comprising a dimer of the formula:

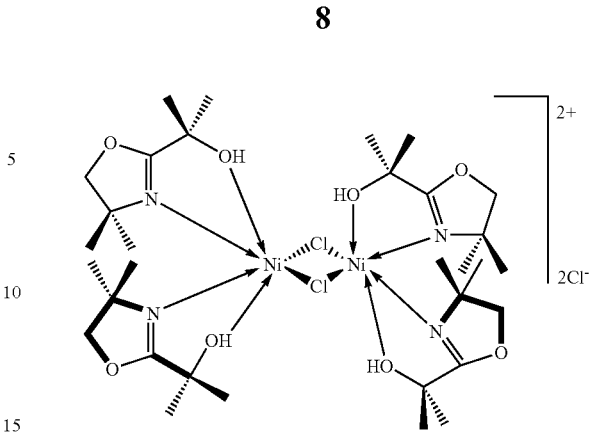

and at least one hydrocarbylaluminum compound which is at least one tris(hydrocarbyl)aluminum compound or at least one aluminoxane.

14. A catalyst composition comprising a dimer of the formula:

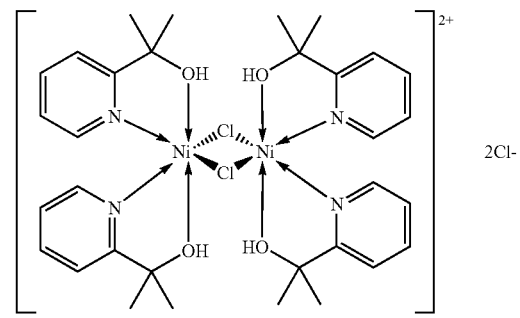

and at least one hydrocarbylaluminum compound which is at least one tris(hydrocarbly)aluminum compound or at least one aluminoxane.

15. A catalyst composition according to claim 1, wherein the hydrocarbylaluminium compound is at least one aluminoxane.

16. A catalyst composition according to claim 14, wherein the hydrocarbylaluminum compound is an aluminoxane or dichloroethylaluminum.

17. A catalyst composition according to claim 13, wherein the hydrocarbylaluminum compound is an aluminoxane or dichloroethylaluminum.

* * * * *